(12) United States Patent
Zur et al.

(10) Patent No.: US 6,178,225 B1
(45) Date of Patent: Jan. 23, 2001

(54) SYSTEM AND METHOD FOR MANAGEMENT OF X-RAY IMAGING FACILITIES

(75) Inventors: Albert Zur, Ganei Tikya; Debra Hakimian, Raanana; Dror Trumer, Hadera, all of (IL)

(73) Assignee: Edge Medical Devices Ltd., Raanana (IL)

(*) Notice: Under 35 U.S.C. 154(b), the term of this patent shall be extended for 0 days.

(21) Appl. No.: 09/325,652

(22) Filed: Jun. 4, 1999

(51) Int. Cl.[7] .................................................. H05G 1/64
(52) U.S. Cl. ............................................................ 378/98.2
(58) Field of Search ............................................. 378/98.2

(56) References Cited

U.S. PATENT DOCUMENTS

| | | |
|---|---|---|
| 4,079,255 | 3/1978 | Brueckner et al. . |
| 4,176,275 | 11/1979 | Korn et al. . |
| 4,539,591 | 9/1985 | Zermeno et al. . |
| 4,961,209 | 10/1990 | Rowlands et al. . |
| 4,975,935 | 12/1990 | Hillen et al. . |
| 4,998,266 | 3/1991 | Hillen et al. . |
| 5,023,455 | 6/1991 | Vanstraelen . |
| 5,059,794 | 10/1991 | Takahashi et al. . |
| 5,077,765 | 12/1991 | Hillen et al. . |
| 5,093,851 | 3/1992 | Schafer . |
| 5,097,493 | 3/1992 | Hillen et al. . |
| 5,117,114 | 5/1992 | Street et al. . |
| 5,153,423 | 10/1992 | Conrads et al. . |
| 5,164,809 | 11/1992 | Street et al. . |
| 5,184,018 | 2/1993 | Conrads et al. . |
| 5,230,927 | 7/1993 | Nishizawa et al. . |
| 5,268,569 | 12/1993 | Nelson et al. . |
| 5,280,512 | 1/1994 | Maack et al. . |
| 5,288,977 * | 2/1994 | Amendolia et al. ................. 378/166 |
| 5,332,893 | 7/1994 | Potts et al. . |
| 5,341,409 | 8/1994 | Conrads et al. . |
| 5,354,982 | 10/1994 | Nelson et al. . |
| 5,369,268 | 11/1994 | Van Aller et al. . |
| 5,396,072 | 3/1995 | Schiebel et al. . |
| 5,436,101 | 7/1995 | Fender et al. . |
| 5,440,146 | 8/1995 | Steffen et al. . |
| 5,467,378 | 11/1995 | Lumma et al. . |
| 5,508,507 | 4/1996 | Nelson et al. . |
| 5,510,626 | 4/1996 | Nelson et al. . |
| 5,519,750 | 5/1996 | Heinemnn et al. . |
| 5,528,043 | 6/1996 | Spivey et al. . |
| 5,530,238 | 6/1996 | Menlenbrugge et al. . |
| 5,563,421 | 10/1996 | Lee et al. . |
| 5,567,929 | 10/1996 | Ouimette . |
| 5,602,889 | 2/1997 | Oldendorf et al. . |
| 5,652,430 | 7/1997 | Lee . |
| 5,686,732 | 11/1997 | Lumma . |
| 5,723,866 | 3/1998 | Hamiltoon, Jr. . |
| 5,729,021 | 3/1998 | Brauers et al. . |
| 5,773,839 | 6/1998 | Krepel et al. . |
| 5,812,191 | 9/1998 | Orava et al. . |
| 5,818,052 | 10/1998 | Elabd . |
| 5,818,053 | 10/1998 | Tran . |
| 5,844,243 | 12/1998 | Lee et al. . |
| 6,084,939 * | 7/2000 | Tamura ................................ 378/98.2 |

* cited by examiner

Primary Examiner—Craig E. Church
(74) Attorney, Agent, or Firm—Pillsbury Madison & Sutro LLP

(57) ABSTRACT

The present invention discloses a system for management of X-ray imaging facilities and services including at least one digital X-ray imaging facility operative to provide digital images in response to X-ray exposures; a metering system associated with each of said at least one digital X-ray imaging facilities for metering the number of digital images produced thereby; and a service center, generating a billing output for each of the at least one digital X-ray imaging facilities in respect of the number of X-ray exposures provided thereby.

20 Claims, 3 Drawing Sheets

SYSTEM AND METHOD FOR MANAGEMENT OF X-RAY IMAGING FACILITIES

FIELD OF THE INVENTION

The present invention relates to systems and methods for management of X-ray imaging facilities and services, specifically digital X-ray imaging facilities.

BACKGROUND OF THE INVENTION

Conventionally, analog film-based X-ray imaging facilities involve initial relatively low equipment costs, particularly when amortized over the fairly long lifetime of the equipment, combined with ongoing significant expenditures per image. Per image expenses include the cost of film, processing, handling, archiving and labor.

Digital X-ray imaging facilities, which are now coming into use, involve equipment costs which are significantly greater than conventional systems and have equipment lifetime that may be shorter than that of a conventional system. The high entry cost of digital X-ray imaging facilities is generally perceived as limiting the widespread use of digital technologies for X-ray imaging. Following initial high equipment costs, digital X-ray facilities are able to offer many benefits including improving diagnostics, savings of time and cost savings by eliminating the film and phosphor screen that are associated with analog imaging, thus significantly streamlining the work flow, enhancing productivity and replacing space-intensive film archives with more easily accessible electronic archives. Moreover, the reduced usage of film and chemicals used for developing and processing of film is expected to offer ecological benefits.

Digital X-ray imaging systems that offer system costs which are competitive with conventional film/screen imaging systems combined with per image costs that are lower than the per image cost of non-digital film/screen systems could lead to widespread penetration of digital X-ray imaging systems to the marketplace, thus accelerating migration of conventional X-ray, the last non-digital medical imaging modality, to digital X-ray imaging.

SUMMARY OF THE INVENTION

There is provided in accordance with a preferred embodiment of the present invention a method for management of X-ray imaging facilities and services including the steps of installing at least a part of a digital X-ray imaging facility; generating digital images corresponding to X-ray exposures; metering the number of X-ray exposures produced by the digital X-ray imaging facility; and generating a billing output in respect of the number of X-ray exposures.

In accordance with a preferred embodiment of the present invention, the metering step of the method for management of X-ray imaging facilities includes taking into account unacceptable exposures.

In further accordance with the present invention, the metering step includes a decision step wherein an operator decides whether to accept an exposure.

In yet further accordance with a preferred embodiment of the present invention, the method for management of X-ray imaging facilities and services also includes an archiving step wherein a generated digital image is retrievably stored.

Moreover, in accordance with a preferred embodiment of the present invention, the archiving step includes transferring the generated digital image to a remote archive.

In still further accordance with a preferred embodiment of the present invention, the metering step includes remote metering via a communications network.

Furthermore, in accordance with a preferred embodiment of the present invention, the remote metering includes communication via e-mail.

Still in accordance with a preferred embodiment of the present invention, the metering step is responsive to at least one characteristic of an X-ray image produced by said facility.

In accordance with a further preferred embodiment of the present invention, the method for management of X-ray imaging facilities and services also includes the step of providing a hard copy of an X-ray image produced by an X-ray exposure.

Moreover, in accordance with yet a further embodiment of the present invention, the method for management of X-ray imaging facilities and services includes the step of preparing a statistical report covering at least some of the X-ray exposures produced by the facility. Information contained in the statistical report may include periodic data regarding the number of accepted exposures, the number of rejected exposures, the overall area, typically, in square inches that was imaged, the number of images printed, dose per image or other data considered relevant to the service center.

There is also provided in accordance with a preferred embodiment of the present invention a system for management of X-ray imaging facilities and services including at least one digital X-ray imaging facility operative to provide digital images in response to X-ray exposures; a metering system associated with each of the digital X-ray imaging facilities for metering the number of digital images produced thereby; and a service center, generating a billing output for each of the digital X-ray imaging facilities in respect of the number of X-ray exposures provided thereby.

Further in accordance with a preferred embodiment of the present invention, the metering system takes into account unacceptable exposures.

Yet further in accordance with the present invention, the metering system is associated with a decision entry interface enabling an operator to decide whether to accept an exposure.

Moreover, in accordance with a preferred embodiment of the present invention, the service center also provides archiving services and generates billing output in accordance thereof.

Still further in accordance with the present invention, the metering system is operative to communicate with the service center via a communications network.

In accordance with the present invention, the metering system may communicate with the service center via an Internet communication technology as described by a Request for Comments (RFC). Alternatively or additionally, the metering system communicates with the service center by electronic polling.

Further in accordance with the present invention, the metering system is responsive to at least one characteristic of an X-ray image produced by the facility. For example, the metering system may be responsive to the number rejected images, accepted images, printed images, stored images or a combination thereof.

Moreover, in accordance with the present invention, the system for management of X-ray imaging facilities and services includes a hard copy output device providing a hard copy of an X-ray image produced by an X-ray exposure.

Yet further in accordance with the present invention, the system for management of X-ray imaging facilities and services also includes a statistical report generator operative to preparing a statistical report covering at least some of the X-ray exposures produced by the facility.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
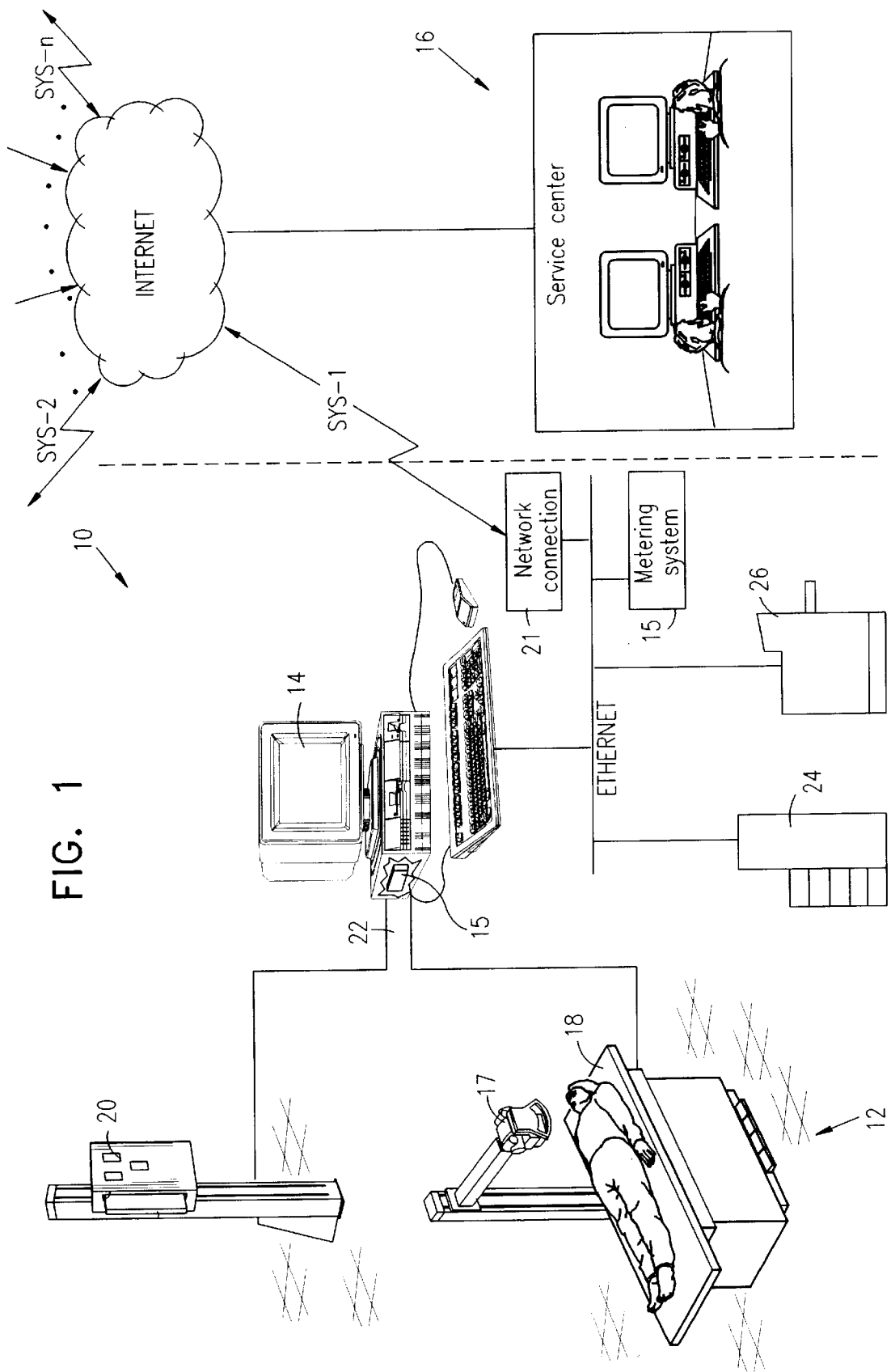
FIG. 1 is a pictorial illustration of a system for management of X-ray imaging facilities and services constructed and operative in accordance with a preferred embodiment of the present invention.

Reference is now made to FIG. 1, which is a diagrammatic view of a digital X-ray image acquisition and management system in accordance with a preferred embodiment of the present invention.

The digital X-ray image acquisition and management system includes at least one digital X-ray imaging facility 10. The digital X-ray imaging facility 10, which may be part of a hospital, private clinic or other X-ray imaging facility and which may form the equivalent of a conventional radiography X-ray room, includes a digital X-ray imaging system 12 and an operating and viewing station 14. The digital X-ray imaging facility 10 preferably includes a metering system 15 for tracking and reporting digital imaging usage statistics to an external service center 16 which handles usage-based billing and other services as described hereinbelow. External service center 16, which is typically associated with the provider of the digital X-ray imaging system 12, may also provide periodic on-site service and maintenance for the digital X-ray imaging system 12.

The digital X-ray imaging system 12, which preferably includes an X-ray generator 17 and a diagnostic radiographic table 18, may also include a digital chest stand 20 towards which X-ray generator 17 is swiveled for imaging thereon.

Suitable digital X-ray systems for digital X-ray imaging system 12 are conventional X-ray systems retrofitted with a digital X-ray detector or integrated systems including a digital X-ray detector, preferably modified to accommodate a metering system and internet connectivity as described herein. Examples of the digital X-ray systems include the DirectRay X-ray capture system that is manufactured and marketed by Sterling Diagnostic Imaging Corporation of Glasgow, Del. or the CXDI-11 manufactured and marketed by Canon Inc. Medical Equipment Group of Japan. Alternatively, the digital X-ray system 12 may include an image detection module as described in applicant's co-pending applications U.S. patent application Ser. No. 09/233,320 filed Jan. 20, 1999 and U.S. patent application Ser. No. 09/233,327 also filed Jan. 20, 1999 which are hereby incorporated by reference.

In accordance with an alternative embodiment of the present invention, digital X-ray imaging system 12 may be any other suitable digital diagnostic X-ray imaging system, such as mammographic or dental systems, which output digital representations of diagnostic transmission modulated X-ray images. It is appreciated that the use of digital X-ray detectors obviates the need for film/screen during X-ray imaging and the post-processing associated therewith.

It is appreciated that, due to the complex solid state electronics and manufacturing costs of digital X-ray systems, the end user price of digital X-ray systems is typically higher than conventional X-ray systems. In accordance with the model described herein, providers of digital X-ray system 12 may supply digital systems at prices which are reduced or competitive with conventional X-ray systems, or alternately, systems may be placed at customer facilities as part of a leasing arrangement. The provider, via the service center 16, receives a revenue stream from imaging procedures performed using the equipment. The user, benefits from "per image" expenses for digital X-ray imaging that are lower than the per image expenses associated with conventional X-ray imaging and film processing, handling etc.

Typically, the metering system 15 includes hardware, software or a combination thereof installed in the operating and viewing station 14, with an electronic backup to ensure accurate and tamper-proof storage of the information. It is appreciated that the metering system may be an integral part of the operating and viewing station 14 or alternately may be an add-on module.

A digital X-ray image of a patient is captured by digital X-ray system 12 and transferred to the control and viewing station 14 using a communications link 22 which may be a conventional wire-based link. Alternately, the communications link may be a fiber optic or wireless link.

Following image capture, the digital X-ray image is calibrated and displayed on the operating and viewing station 14 and viewed by a technologist.

After the technologist has viewed the image, the image may be exported from operating and viewing station 14 and stored at a local archive 24 where it is retrieved for diagnostics. It is appreciated that local archive 24 may be part of a Picture Archiving and Communication System (PACS). Preferably transfer of files from the operating and viewing station 14 is handled using the Digital Imaging and COmmunications in Medicine (DICOM) standard. Alternatively, any other compatible standard may be used.

When desired, a hard copy of the X-ray image may be printed using hard copy output device 26 which may be a "dry" laser imager such as the Dryview 8700 Laser Imaging System manufactured by the Eastman Kodak Company of Rochester, N.Y. or a "wet" laser image such as the Agfa SCOPIX LR 5200 offered by the Medical Imaging Systems, Agfa Division, Bayer Corporation. Alternatively, images may be stored on a portable electronic storage media e.g. a writable compact disc (not shown).

In accordance with a preferred embodiment of the present invention, the digital X-ray imaging facility 10 has internet connectivity via a direct modem connection or via a network connection 21.

As an alternative to local archive 24, secure archiving services for the digital X-ray imaging facility 10 may be provided by the service center 16. In accordance with this embodiment, in addition to the metering system, the operating and viewing station 14 also includes a software module that allows "lossless" compression and decompression of imaging files and DICOM based transfer/retrieval thereof, e.g. via the Internet, to/from a remote archive at the service center 16, as known in the art. It is appreciated that transfer to the archive may take place at any convenient time after imaging and does not have to occur immediately following exposure.

As an alternative to hard copy output device 26, printing services (not shown) for the digital X-ray imaging facility 10 may be provided by the service center 16. In accordance with this embodiment, imaging files are transferred to the service center 16 as described above and printed by a high quality laser imager at a central printing facility (not shown). The "printed" images are then shipped via overnight mail, e.g. Federal Express, to the desired destination.

This provides the digital X-ray imaging facility 10 with the economic advantage of avoiding the purchase of a high quality laser imager, which in addition to the system expense, generally requires plumbing and waste handling due to the chemicals involved, or of an expensive "dry" printer with its associated high consumables cost.

Printing and archiving services as described herein are particularly suited to the large base of smaller clinics and enterprises which may not have enough initial business to justify significant upfront expenses required in establishing a digital X-ray imaging practice.

The service center 16 which is preferably accessible via the Internet receives, automatically or manually, usage statistics from the metering systems (not shown) of a plurality of digital X-ray image facilities, referred to in FIG. 1 as SYS-1 to SYS-n. It is appreciated that the systems (SYS-1 to SYS-n) may have a wide geographic distribution. Service center 16 may include a distributed network of local servers or alternately may include a centralized service location. Alternatively, the service center 16 may be accessible directly using conventional communication lines and standard communication protocols.

Based on the information from the usage statistics and a pricing schedule, the service center 16 periodically generates and distributes billing statements to the entities served by the X-ray image acquisition and management systems.

Figure 2:
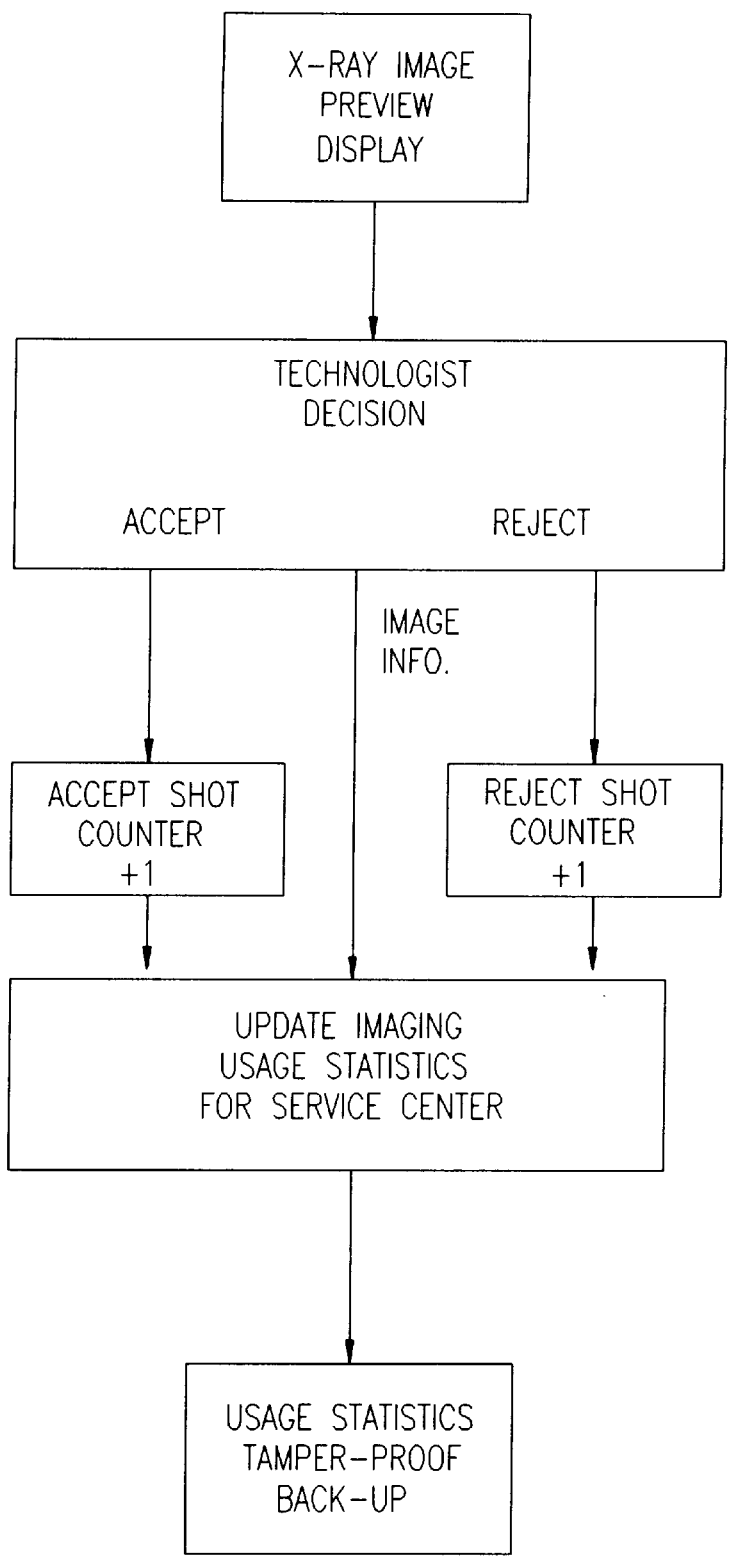
FIG. 2 is a simplified functional block diagram of a preferred embodiment of the system of FIG. 1.

Reference is now made to FIG. 2 which describes the operation of the metering system 15 of digital X-ray imaging facility 10 in accordance with a preferred embodiment of the present invention. The metering system 15 preferably works as follows:

Electronically generated X-ray images are displayed on the operating and viewing station 14 (FIG. 1) for a preview display.

In accordance with a preferred embodiment of the present invention, the technologist may decide whether to accept or reject the X-ray image. If the image is accepted, then an accept shot counter is incremented by one. If the shot is rejected, then a rejected shot counter is incremented by one. Depending on the specific arrangement with the site operating the digital X-ray image acquisition and management system 10, the service center 16 may record and bill for rejected images at the same rate as accepted images. Alternatively, accepted images may be dealt with separately from rejected ones. According to one embodiment of the invention, if the image is displayed on the operator console for more then a predefined period of time or if the image is printed or stored, the image is automatically considered accepted and the accept shot counter is incremented by one.

The accept or reject criterion is based on the technologist's professional evaluation of the image and his decision whether or not the image needs to be retaken. Typically, accepted images are forwarded to an archive for storage and subsequent retrieval by the radiologist who will diagnose the patient who was imaged. Alternatively, images may be printed as a hard copy which may be stored in a standard film archive.

In addition to accept and reject shot counters, the metering system 15 preferably tracks imaging parameters for each shot. Examples of imaging parameters are the area that was imaged and the size of the file representing the image, which may vary in accordance with the area being imaged or the resolution of the imaging.

The usage statistics stored by the metering system 15 are periodically updated to the service center 16 by any of the update methods described hereinbelow with respect to FIG. 3.

Figure 3:
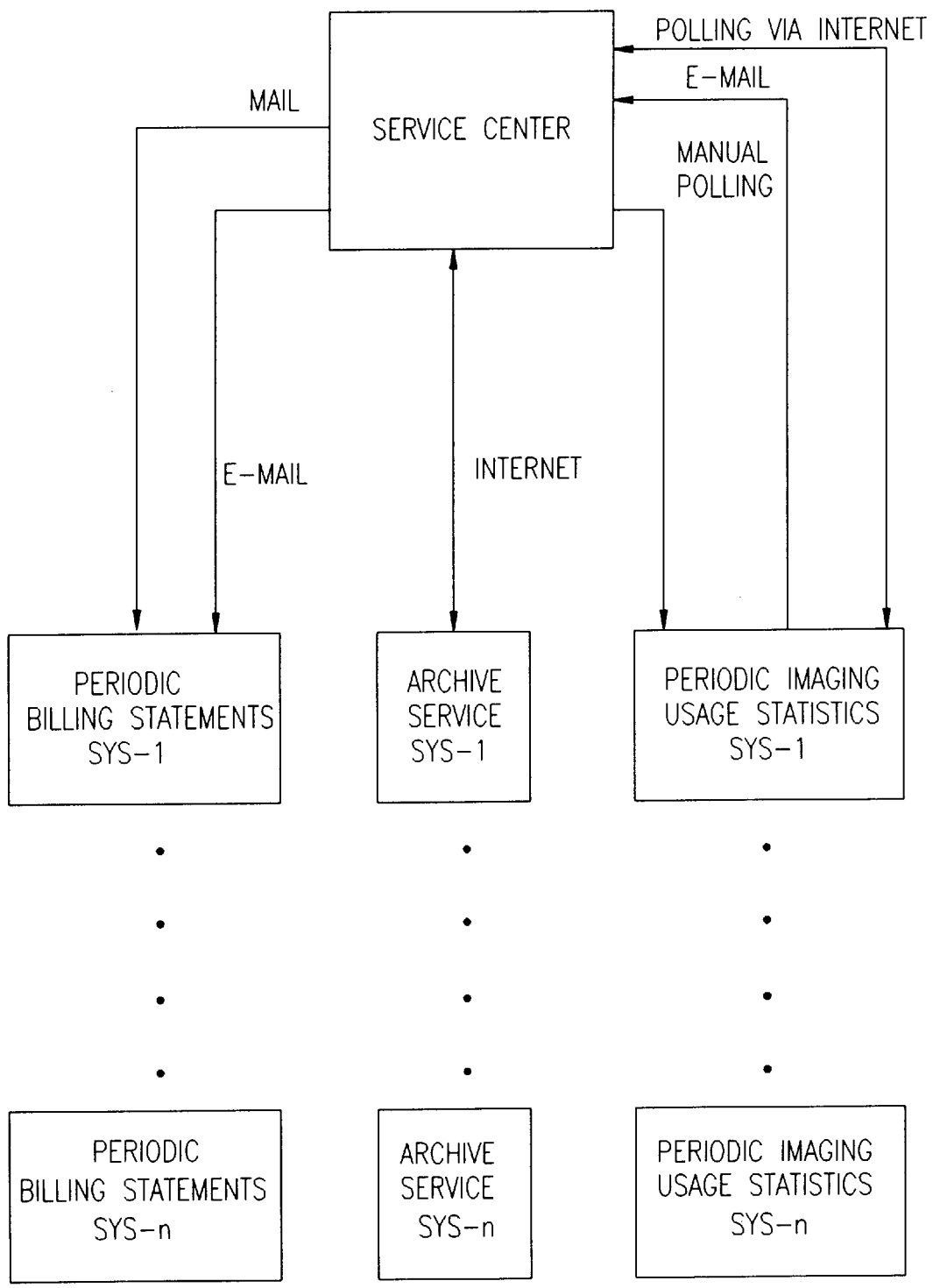
FIG. 3 is a simplified block diagram illustrating the operation of part of the system of FIG. 1 in accordance with a preferred embodiment of the present invention.

Reference is now additionally made to FIG. 3 which is a block diagram illustrating the operation of the service center 16 of FIG. 1 in accordance with a preferred embodiment of the present invention.

The service center 16 periodically receives usage statistics from the metering systems, such as the metering system 15 of FIG. 1, of a plurality of digital X-ray imaging facilities and management systems as described hereinabove.

Communication between the service center 16 and the individual metering systems may be via any standard Internet communications technology, as typically described in Request for Comments (RFC) documents, such as electronic mail (e-mail). E-mail reports, which may be sent as attached files, are preferably automatically initiated on a regularly scheduled basis, e.g. daily, weekly or monthly, by the operating and viewing station 14 of each digital X-ray imaging facility 10 and sent to the service center 16.

It is appreciated that usage statistics can be sent via e-mail since the information being transmitted is not of a highly confidential nature and does not require secure lines for transmission. Moreover, the electronic backup present in the operating and viewing station 14 allows for information received via e-mail to be cross-checked and verified by a service technician during periodic maintenance visits.

The use of e-mail for communications is widely known and is suitable for large organizations having a private network which is protected from the Internet by a firewall, since sending or receiving e-mail does not breach the firewall security. The use of e-mail for communication is also suited to small organizations which use modems for internet connectivity, with updates sent in accordance with the users' own log-on schedule.

In accordance with alternate embodiments of the present invention, the service center 16 may electronically poll individual digital X-ray imaging facilities 10 to periodically update the usage statistics. This approach may necessitate access to an internal network via a password or code or alternately, a less favorable approach requiring a dedicated separate communication line between the service center 16 and the digital X-ray imaging facility 10.

In the case of digital X-ray imaging facilities which are not connected to the Internet, the service center 16 can manually poll via telephone or fax to receive updates for the usage statistics for the remote system. Alternatively, the usage statistics stored in the tamper-proof backup can be read by a service technician during a periodic maintenance visit.

When e-mail is used for correspondence, it is appreciated that periodic billing and usage statements may be issued by the service center 16 to digital X-ray imaging facilities via e-mail. Alternatively or additionally, billing and usage statements may be distributed by mail.

In accordance with an alternative embodiment of the present invention, service center 16 may also offer archiving services to digital X-ray imaging facilities which have Internet connectivity. This approach, which would allow fee-based storage and retrieval of images, would provide users, who may typically be computer novices, an alternative to the establishment of an on-site archive and backup system, thus further reducing the installation costs of digital X-ray systems.

Other services that may be provided by the service center 16 are hard copy print out as described hereinabove.

In accordance with the invention, the intent of the value-added services is to further reduce the entry cost of digital X-ray imaging to end users thus enabling wider use and adaptation of digital X-ray imaging technologies.

It will be appreciated by persons skilled in the art that the present invention is not limited by what has been described above. The scope of the present invention includes both combinations and sub-combinations of the various features described hereinabove as well as modifications and additions thereto which would occur to a person skilled in the art upon reading the foregoing disclosure and which are not in the prior art.

What is claimed is:

1. A method for management of X-ray imaging facilities and services comprising the steps of:

installing at least a part of a digital X-ray imaging facility;

generating digital images corresponding to X-ray exposures;

metering the number of X-ray exposures produced by said digital X-ray imaging facility; and generating a billing output in respect of the number of X-ray exposures.

2. A method for management of X-ray imaging facilities and services according to claim 1 and wherein the metering step includes taking into account unacceptable exposures.

3. A method for management of X-ray imaging facilities and services according to claim 2 and wherein said metering step includes a decision step wherein an operator decides whether to accept an exposure.

4. A method for management of X-ray imaging facilities and services according to claim 1 and also including an archiving step wherein a generated digital image is retrievably stored.

5. A method for management of X-ray imaging facilities according to claim 4 wherein the archiving step includes transferring the generated digital image to a remote archive.

6. A method for management of X-ray imaging facilities and services according to claim 1 and wherein the metering step comprises remote metering via a communications network.

7. A method for management of X-ray imaging facilities and services according to claim 6 and wherein the remote metering includes communication via e-mail.

8. A method for management of X-ray imaging facilities and services according to claim 1 and wherein the metering step is responsive to at least one characteristic of an X-ray image produced by said facility.

9. A method for management of X-ray imaging facilities and services according to claim 1 and also comprising the step of providing a hard copy of an X-ray image produced by an X-ray exposure.

10. A method for management of X-ray imaging facilities and services according to claim 1 and also comprising the step of preparing a statistical report covering at least some of the X-ray exposures produced by the facility.

11. A system for management of X-ray imaging facilities and services comprising:

at least one digital X-ray imaging facility operative to provide digital images in response to X-ray exposures;

a metering system associated with each of said at least one digital X-ray imaging facilities for metering the number of digital images produced thereby; and a service center, generating a billing output for each of the at least one digital X-ray imaging facilities in respect of the number of X-ray exposures provided thereby.

12. A system for management of X-ray imaging facilities and services according to claim 11 and wherein the metering system takes into account unacceptable exposures.

13. A system for management of X-ray imaging facilities and services according to claim 12 and wherein the metering system is associated with a decision entry interface enabling an operator to decide whether to accept an exposure.

14. A system for management of X-ray imaging facilities and services according to claim 11 and wherein said service center also provides archiving services and generates billing output in accordance thereof.

15. A system for management of X-ray imaging facilities and services according to claim 11 and wherein the metering system is operative to communicate with the service center via a communications network.

16. A system for management of X-ray imaging facilities and services according to claim 15 and wherein the metering system communicates with the service center via an internet communication technology as described by a Request for Comment document.

17. A system for management of X-ray imaging facilities and services according to claim 15 and wherein the metering system communicates with the service center by e-mail.

18. A system for management of X-ray imaging facilities and services according to claim 11 and wherein the metering system is responsive to at least one characteristic of an X-ray image produced by said facility.

19. A system for management of X-ray imaging facilities and services according to claim 11 and also comprising a hard copy output device providing a hard copy of an X-ray image produced by an X-ray exposure.

20. A system for management of X-ray imaging facilities and services according to claim 11 and also comprising a statistical report generator operative to preparing a statistical report covering at least some of the X-ray exposures produced by the facility.

* * * * *